(12) United States Patent
Wefler

(10) Patent No.: US 7,462,329 B2
(45) Date of Patent: Dec. 9, 2008

(54) AUTOMOBILE AIR FRESHENING SYSTEM

(75) Inventor: Mark E. Wefler, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 351 days.

(21) Appl. No.: 11/146,600

(22) Filed: Jun. 7, 2005

(65) Prior Publication Data
US 2005/0271371 A1 Dec. 8, 2005

Related U.S. Application Data

(60) Provisional application No. 60/577,212, filed on Jun. 7, 2004.

(51) Int. Cl.
A61L 9/12 (2006.01)
(52) U.S. Cl. .................................... 422/124
(58) Field of Classification Search ....................... None
See application file for complete search history.

(56) References Cited

U.S. PATENT DOCUMENTS

| | | | |
|---|---|---|---|
| 4,702,418 A | 10/1987 | Carter et al. | |
| 4,814,212 A | 3/1989 | Spector | |
| 4,869,407 A | 9/1989 | Booth, Jr. et al. | |
| 4,961,885 A | 10/1990 | Avrahami et al. | |
| 4,968,456 A | 11/1990 | Muderlak et al. | |
| 5,048,733 A | 9/1991 | Nagy | |
| 5,060,864 A | 10/1991 | Nishi et al. | |
| 5,192,342 A | 3/1993 | Baron et al. | |
| 5,339,638 A | 8/1994 | Kessel | |
| 5,805,768 A | 9/1998 | Schwartz et al. | |
| 5,833,929 A | 11/1998 | Watson et al. | |
| 5,906,509 A | 5/1999 | Wu | |
| 6,008,732 A | 12/1999 | Lam | |
| 6,021,254 A | 2/2000 | Hunter | |
| 6,102,660 A * | 8/2000 | Lee ........................ | 416/146 R |
| 6,140,934 A | 10/2000 | Lam | |
| 6,254,065 B1 | 7/2001 | Ehrensperger et al. | |
| 6,293,474 B1 | 9/2001 | Helf et al. | |
| 6,296,196 B1 | 10/2001 | Denen et al. | |
| 6,471,193 B2 * | 10/2002 | Cole Warren ................ | 261/27 |
| 6,551,142 B2 | 4/2003 | Eisenbraun | |
| 6,554,203 B2 | 4/2003 | Hess et al. | |
| 6,581,915 B2 | 6/2003 | Bartsch et al. | |
| 6,592,828 B2 | 7/2003 | Quintana Munoz | |
| 2002/0176704 A1 | 11/2002 | Roe | |
| 2003/0102384 A1 | 6/2003 | Walter et al. | |
| 2003/0192959 A1 | 10/2003 | Hess et al. | |
| 2004/0003724 A1* | 1/2004 | Ellis ........................... | 96/115 |
| 2004/0033171 A1 | 2/2004 | Kvietok et al. | |

FOREIGN PATENT DOCUMENTS

| | | |
|---|---|---|
| DE | 10328965 | 2/2005 |
| JP | 11278048 | 10/1999 |
| WO | WO 03/077961 A1 | 9/2003 |
| WO | WO2004096297 A1 * | 11/2004 |

* cited by examiner

Primary Examiner—Elizabeth L McKane

(57) ABSTRACT

An automobile air freshening system having a piezoelectric atomizer unit (1) and a canister assembly (11) insertable in the piezoelectric atomizer unit (1). The piezoelectric atomizer unit (1) may include a temperature sensor, a programming unit, an active ingredient intensity selection switch (13), a boost override button, or any combination thereof.

9 Claims, 5 Drawing Sheets

AUTOMOBILE AIR FRESHENING SYSTEM

This application claims the benefit of U.S. Provisional Application No. 60/577,212 filed on Jun. 7, 2004.

BACKGROUND OF THE INVENTION

I. Field of the Invention

This invention relates to an automobile air freshening system preferably comprising a piezoelectric atomizer unit operating within the confines of an automobile, and a canister assembly. In particular, the invention relates to a piezoelectric atomizer unit that releases an active ingredient, such as a fragrance, deodorizer, or the like, from the canister assembly into the interior airspace of the automobile. The atomizer unit may include features such as a fragrance intensity slide switch, a programming unit, a temperature sensor, a boost override button, and any combination thereof.

II. Description of the Related Art and Problem to be Solved

Devices that release a fragrance into the interior airspace of an automobile are well known in the art. Generally, the purpose of these devices is to deodorize or impart a desired fragrance to the interior airspace.

In some systems, a device that slowly releases a fragrance into the atmosphere is placed inside the automobile. For example, U.S. Pat. No. 4,814,212 discloses that an air freshener unit is adhered to the inner surface of an automobile window and that the unit slowly releases a fragrance into the atmosphere.

Systems such as the one described in U.S. Pat. No. 4,814,212 have several limitations. For example, the user is not able to select when fragrance will be released from the device, nor the amount of fragrance to be released from the device. Additionally, the device does not account for fluctuations in the air temperature of the automobile. Thus, when the interior of the automobile gets warm, the interior airspace of the automobile may become suffused with too much fragrance.

The present invention is an attempt to solve the above-noted limitations of automobile air freshening systems, which release an active ingredient, such as a fragrance, deodorizer, or the like. While a number of active ingredients are contemplated, we refer to fragrances in our discussion of the preferred embodiments, for explanatory purposes.

SUMMARY OF THE INVENTION

Generally, the present invention is directed to an automobile air freshening system.

In one aspect, the automobile air freshening system includes a piezoelectric atomizer unit for releasing an active ingredient from a canister assembly when the canister assembly is mated therewith. The air freshening system also includes a controller for controlling periodic activation of the atomizer unit to release the active ingredient, and an adapter engageable with a 12-volt DC current power outlet in an automobile provides power to the controller and the atomizer unit.

Preferably, the system further includes a temperature sensor for sensing a temperature and relaying the sensed temperature to the controller. The controller controls a delivery rate of the active ingredient based on the sensed temperature.

Preferably, the system further includes a programming unit for selectably controlling a time for starting the system and a time for stopping the system. During a time period between the system start time and the system stop time, the controller periodically activates the atomizer unit to release the active ingredient. The programming unit may also selectably control the delivery rate of the active ingredient during a time period between the system start time and the system stop time.

Preferably, the system further includes a boost override button, which causes the controller to activate the atomizer unit to release the active ingredient contemporaneously with activation of the boost override button.

In a second aspect, the automobile air freshening system includes a piezoelectric atomizer unit for releasing an active ingredient from a canister assembly when the canister assembly is mated therewith. The air freshening system also includes a controller for controlling periodic activation of the atomizer unit to release the active ingredient, and a temperature sensor for sensing a temperature and relaying the sensed temperature to the controller. The controller controls a delivery rate of the active ingredient based on the sensed temperature.

Preferably, the system further includes a programming unit for selectably controlling a time for starting the system (i.e., active ingredient delivery) and a time for stopping the system. During a time period between the system start time and the system stop time, the controller periodically activates the atomizer unit to release the active ingredient. The programming unit may also selectably control the delivery rate of the active ingredient during a time period between the system start time and the system stop time.

Preferably, the system further includes a boost override button, which causes the controller to activate the atomizer unit to release the active ingredient contemporaneously with activation of the boost override button.

In a third aspect, the automobile air freshening system includes a piezoelectric atomizer unit for releasing an active ingredient from a canister assembly when the canister assembly is mated therewith. The air freshening system also includes a controller for controlling periodic activation of the atomizer unit to release the active ingredient and a programming unit for selectably controlling a time for starting the system and a time for stopping the system. During a time period between the system start time and the system stop time, the controller periodically activates the atomizer to release the active ingredient.

Preferably, the programming unit also selectably controls the delivery rate of the active ingredient during a time period between the system start time and the system stop time.

Preferably, the system further includes a boost override button, which causes the controller to activate the atomizer unit to release the active ingredient contemporaneously with actuation of the boost override button.

Preferably, the system further includes an active ingredient intensity selection switch for adjusting the frequency at which said controller activates said atomizer unit to release the active ingredient.

DETAILED DESCRIPTION OF THE INVENTION

Air freshening systems utilizing piezoelectric atomizer units are known in the art. Regarding the specific construction of the piezoelectric atomizer unit, reference is made herein to U.S. Pat. No. 6,293,474, U.S. Pat. No. 6,296,196, U.S. Pat. No. 6,341,732, U.S. Pat. No. 6,439,474, U.S. Pat. No. 6,446,880, U.S. Pat. No. 6,450,419 and U.S. Pat. No. 6,857,580, the disclosures of which are incorporated herein by reference.

Generally, the automobile air freshening system of the present invention includes a piezoelectric atomizer unit that releases a puff of fragrance from a fragrance canister assembly mated therewith. A controller periodically activates the atomizer unit causing a puff of fragrance to be released into the interior airspace of the automobile. The interval, for example, may be one puff every 30 seconds. In this manner, over time, the airspace of the automobile becomes suffused with the fragrance.

Figure 1:
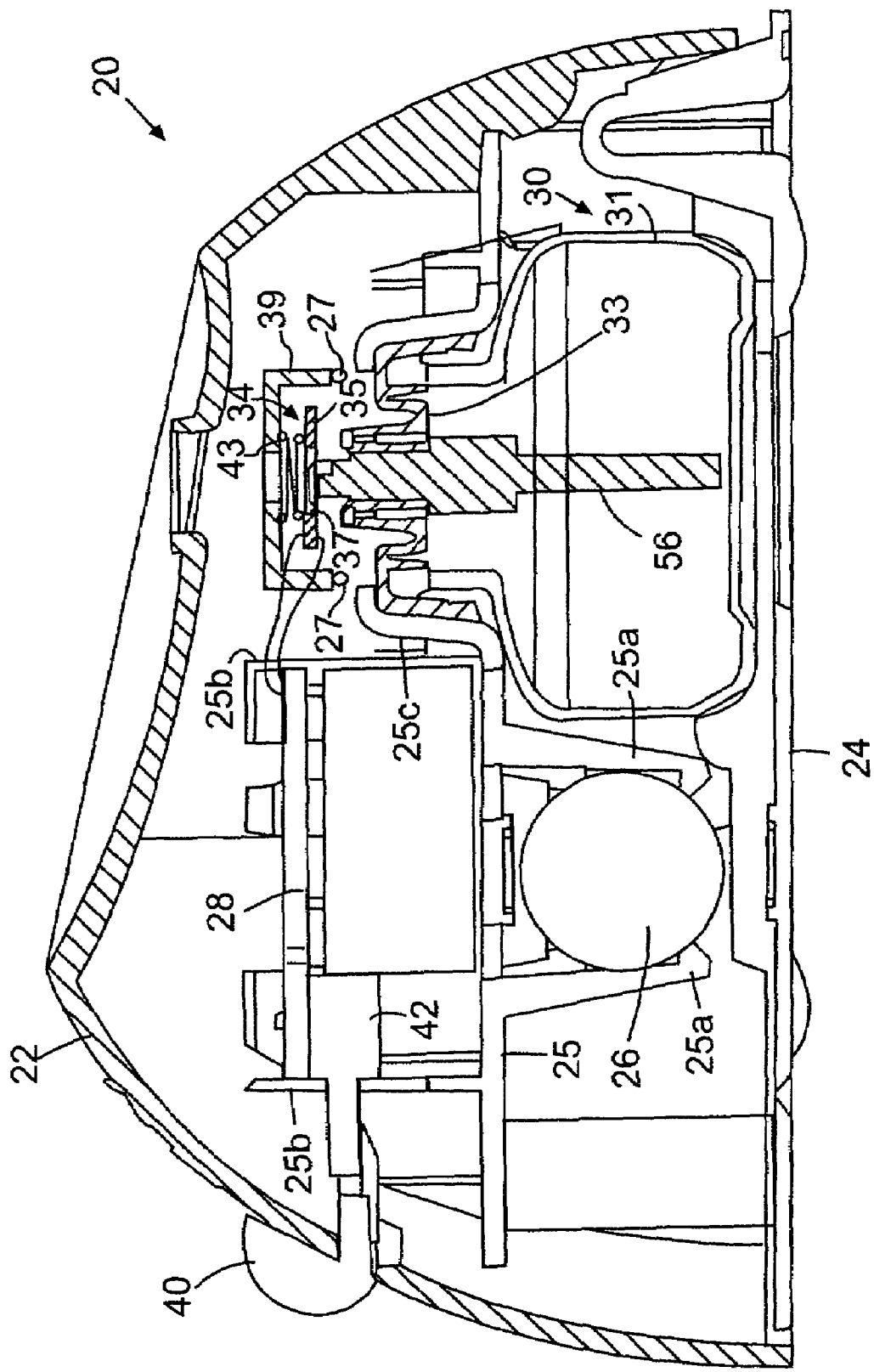
FIG. 1 shows an elevated cross section of a piezoelectric atomizer unit.

A specific example of the construction of a battery-powered piezoelectric atomizer unit is depicted in FIG. 1. As shown in FIG. 1, an atomizer unit 20 may comprise an atomizer assembly 34, which includes an orifice plate 37, and a replaceable fragrance canister assembly 30. The fragrance canister assembly 30 includes a fragrance canister 31 containing fluid and a wick 56.

The piezoelectric atomizer device 20 depicted in FIG. 1 includes a housing 22 formed as a hollow plastic shell and closed by a flat bottom wall 24. A horizontal platform 25 extends across the interior of the housing 22. A battery 26 is supported by means of support prongs 25a that extend down from the underside of the platform 25 inside the housing 22. In other embodiments, an adapter that engages with a cigarette lighter or auxiliary power outlet of an automobile may replace the battery. In addition, a printed circuit board 28 is supported on support elements 25b that extend upwardly from the platform 25. A fragrance canister assembly 30 is replaceably mounted to the underside of a dome-like formation 25c on the platform 25.

The fragrance canister assembly 30 comprises a fragrance canister 31 for holding a fragrance to be atomized, a plug 33, which closes the top of the container, and the wick 56, which extends from within the fragrance canister 31 through the plug 33, to a location above the fragrance canister 31. The plug 33 is constructed to allow removal and replacement of the complete fragrance canister assembly 30 from the underside of the dome-like formation 25c on the platform 25. Preferably, the plug 33 and the platform are formed with a bayonet attachment (not shown) for this purpose. It could also be attached by means of a screw thread, snap attachment or any other means to locate and position the fragrance canister assembly next to the dome-like formation. When the replaceable fragrance canister assembly 30 is mounted on the platform 25, the wick 56 extends up through a center opening in the dome-like formation 25c. The wick 56 operates by capillary action to deliver liquid from within the fragrance canister 31 to a location just above the dome-like formation 25c on the platform 25.

An atomizer assembly 34 is supported on the platform 25 in cantilever fashion by means of a resilient, elongated wire-like support 27. The wire-like support 27 is attached at the ends, which protrude upward from the platform 25. The wire-like support 27 is shaped such that it resiliently supports the lower surface of the orifice plate 37 and a spring housing 39, while a spring 43 resiliently presses on the upper surface of the orifice plate 37. (Rather than press on the orifice plate 37 itself, the spring 43 may alternatively or additionally press on a member, such as an actuator element 35, discussed below, which is connected to the orifice plate 37.) Together, the support 27 and the spring 43 hold the orifice plate 37 in place in a manner that allows the orifice plate 37 to move up and down against the resilient bias of the wire-like support 27.

The atomizer assembly comprises an annularly shaped piezoelectric actuator element 35 and the circular orifice plate 37, which extends across and is soldered or otherwise affixed to the actuator element 35. When alternating voltages are applied to the opposite upper and lower sides of the actuator element 35 these voltages produce electrical fields across the actuator element 35 and cause it to expand and contract in radial directions. This expansion and contraction is communicated to the orifice plate 37 causing it to flex so that a center region thereof vibrates up and down. The center region of the orifice plate 37 is domed slightly upward to provide stiffness and to enhance atomization. The center region is also formed with a plurality of minute orifices that extend through the orifice plate 37 from the lower or under surface of the orifice plate 37 to its upper surface. A flange is provided around the center region of the dome.

In operation, the battery 26 supplies electrical power to circuits on the printed circuit board 28 and these circuits convert this power to high frequency alternating voltages. A suitable circuit for producing these voltages is shown and described in U.S. Pat. No. 6,296,196. As described in that patent, the device may be operated such that fragrance is released at a specified interval. The interval can be adjusted by a fragrance intensity selection switch 40 on the outside of the housing 22 and coupled to a switch element 42 on the printed circuit board 28.

When the atomizer assembly 34 is supported by the support member 27, the flange of the orifice plate 37 is positioned in contact with the upper end of the wick 56. The atomizer assembly 34 is thereby supported above the fragrance canister assembly 30 such that the upper end of the wick 56 touches the underside of the orifice plate 37. Thus, the wick 56 delivers liquid from within the fragrance canister 31 by capillary action to the underside of the orifice plate 37, which upon vibration, causes the liquid to pass through its orifices and be ejected from its opposite side (i.e., the upper surface) in the form of very small droplets, leading to a puff of fragrance.

It will be appreciated from the foregoing that the horizontal platform 25 serves as a common structural support for both the fragrance canister assembly 30 and the atomizer assembly 34. Thus, the horizontal platform maintains the fragrance canister assembly 30, and particularly, the upper end of the wick 56, in alignment with the orifice plate 37 of the atomizer assembly 34. Moreover, because the atomizer assembly 34 and the orifice plate 37 are resiliently mounted, the upper end of the wick 56 preferably presses against the under surface of the orifice plate 37 and/or the actuator element 35 irrespective of dimensional variations which may occur due to manufacturing tolerances when one fragrance canister assembly is replaced by another. This is because if the wick 56 of the replacement fragrance canister assembly 30 is higher or lower than the wick 56 of the original fragrance canister assembly 30, the action of the spring 43 will allow the orifice plate 37 to move up and down according to the location of the wick 56 in the replacement fragrance canister assembly 30, so that the wick 56 will properly press against the underside of the orifice plate 37 and/or the actuator element 35. It will be appreciated that the wick 56 preferably is formed of a solid, dimensionally stable material so that it will not become deformed when pressed against the underside of the resiliently supported orifice plate 37.

Figure 2:
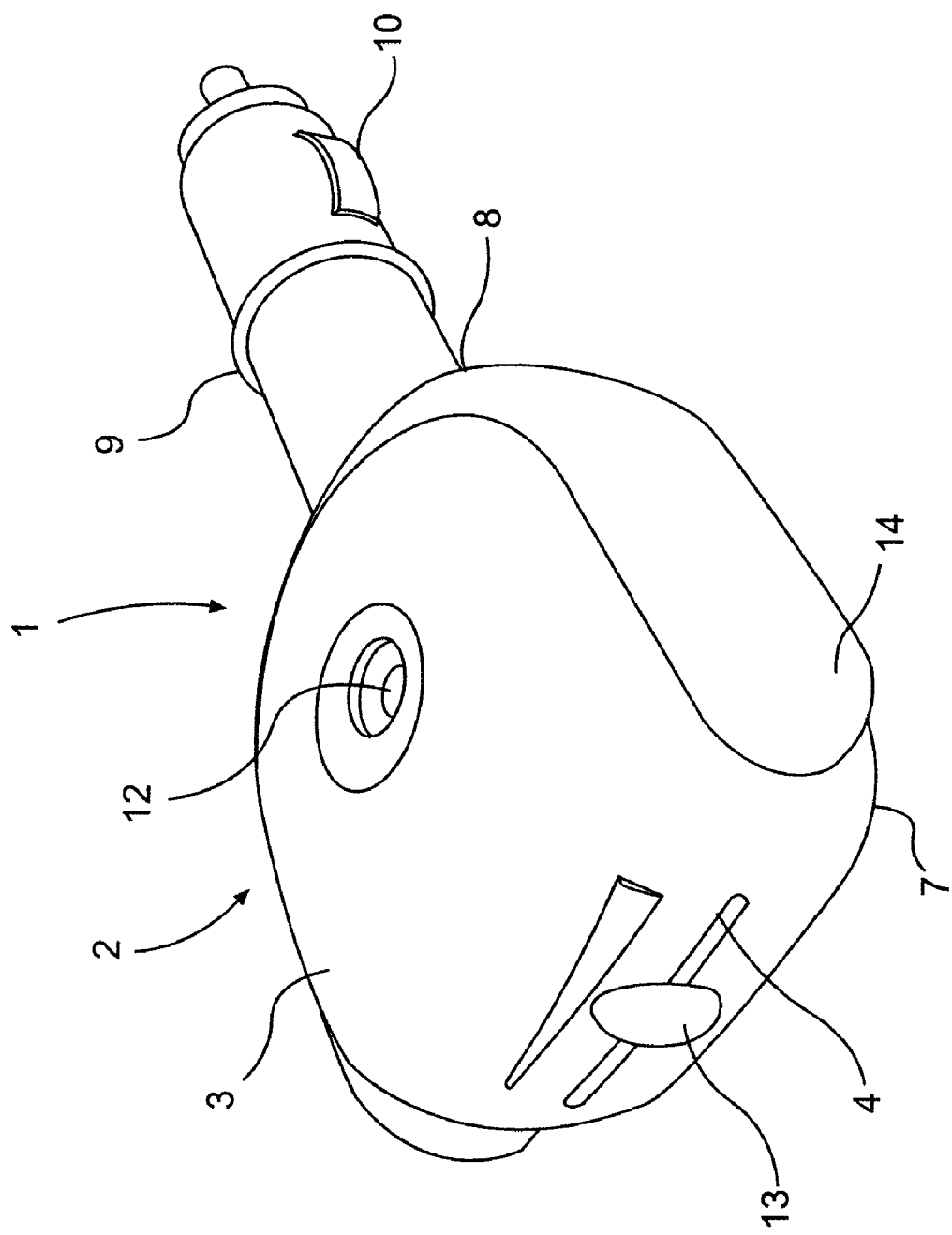
FIG. 2 is a view of one embodiment of the automobile air freshening system of the present invention.
Figure 2:
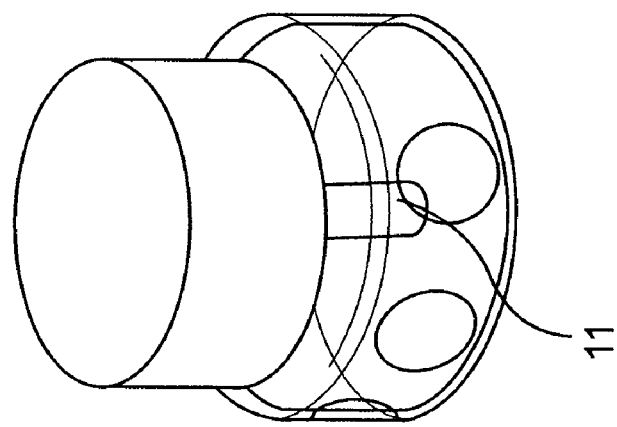

FIG. 2 depicts one embodiment of the present invention. The atomizer unit 1 of this embodiment has an outer housing 2 including a top 3, front 4, bottom 7, and back 8. Protruding from the back 8 is an adapter 9. Adapter 9 engages with a cigarette lighter or auxiliary power outlet of the automobile via electrical connection point 10. There is an additional electrical connection point (not shown) on the adapter directly opposite from electrical connection point 10. In this manner, the atomizer unit utilizes the 12-volt DC current from the electrical system of the automobile as a power supply. A fragrance canister assembly 11 is removably insertable into the atomizer unit through an insertion slot (not shown) in the bottom 7 of the unit. Once the fragrance canister assembly 11 is properly positioned inside the atomizer unit, fragrance is emitted through a hole 12 in the top 3 of the atomizer unit. Mounted into the front 4 of the atomizer unit is a fragrance intensity selection switch 13, which may be actuated by a user to increase or decrease the frequency at which the atomizer unit releases fragrance.

Additionally, in this embodiment, the adapter 9 supports outer housing 2 at hinge point 14. This configuration allows the portion of the atomizer unit containing the fragrance canister assembly to be placed in an upright position to help prevent the fragrance canister assembly from leaking. This is particularly useful in accommodating auxiliary power outlets with different angles of orientation. The hinge point may be configured such that the position of the portion of the atomizer unit containing the fragrance canister assembly 11 relative to the adapter 9 is adjustable by the user. Alternatively, the portion containing the fragrance canister assembly may be free floating on hinge point 14, such that the relative position of the portion of the atomizer unit containing the fragrance canister assembly is maintained in an upright position due to the force of gravity.

Use of the adapter 9 is advantageous because the atomizer unit would, in most cases, not operate when the automobile is not operating, thus preventing a buildup of fragrance that could be overwhelming when first entering the automobile. Use of the adapter also eliminates the need for costly batteries and the need to replace and/or dispose of batteries periodically.

Figure 3:
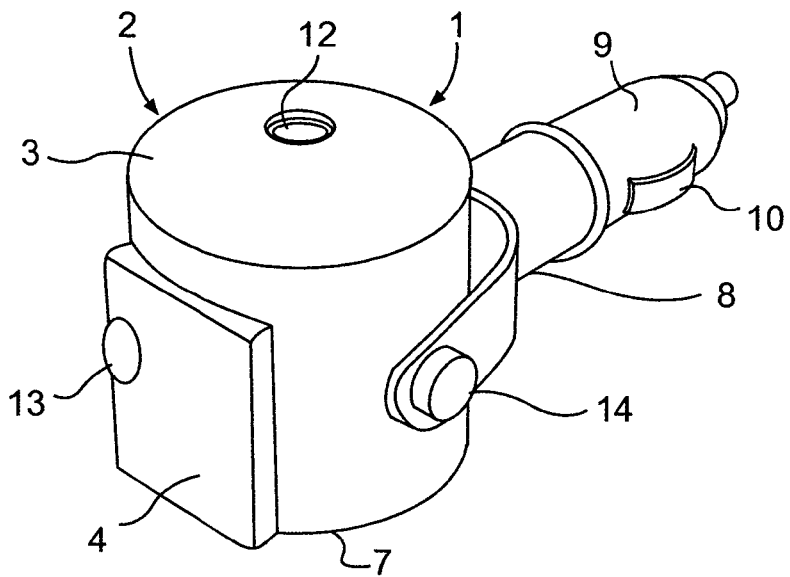
FIG. 3 is a view of a second embodiment of the automobile air freshening system of the present invention.
Figure 4:
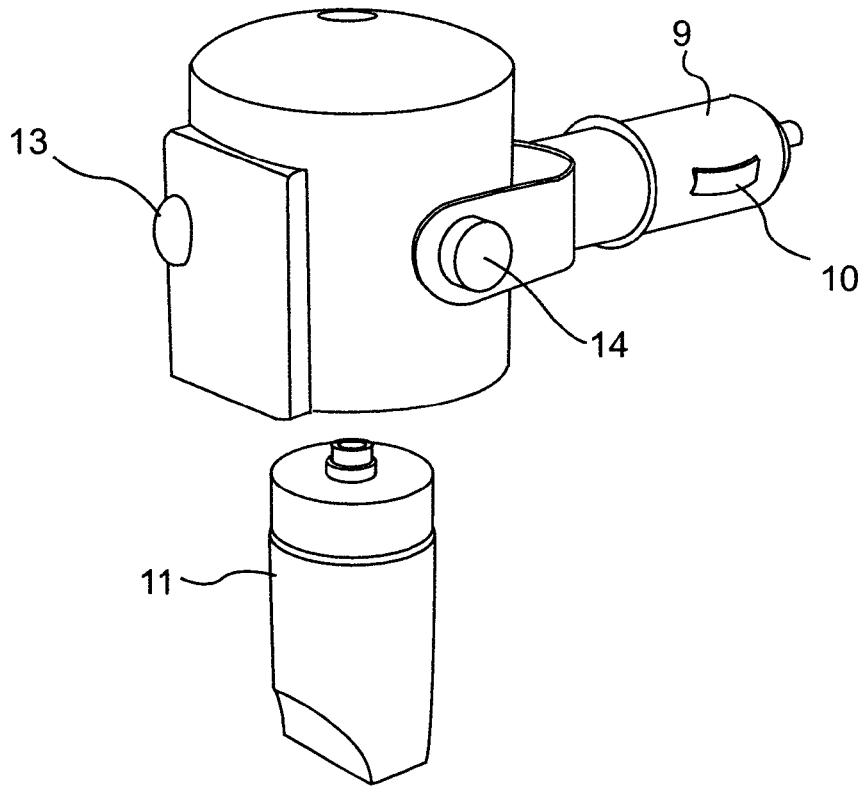
FIG. 4 is a view of the second embodiment of the automobile air freshening system showing the piezoelectric atomizer unit (1) and the fragrance canister assembly (11).

FIGS. 3 and 4 depict a second embodiment of the present invention. As with the first embodiment, the atomizer unit 1 has an outer housing 2 including a top 3, front 4, bottom 7 and back 8. A fragrance canister assembly 11 is removably insertable into the atomizer unit through an insertion slot (not shown) in the bottom 7 of the unit. Once the fragrance canister assembly 11 is properly positioned inside the atomizer unit, fragrance is periodically released through a hole 12 in the top 3 of the atomizer unit. Mounted into the front of the atomizer unit is a fragrance intensity selection switch 13. By actuating the switch, the user is able to increase or decrease the frequency at which the atomizer unit releases fragrance.

Additionally, in this second embodiment of the present invention, protruding from the back 8 is an adapter 9 that engages with a cigarette lighter or auxiliary power-outlet of the automobile via electrical connection point 10. In this embodiment, the adapter 9 supports outer housing 2 at hinge point 14. This configuration allows the portion of the atomizer unit containing the fragrance cartridge to be placed in an upright position to help prevent the fragrance canister assembly 11 from leaking. This is particularly useful in accommodating auxiliary power outlets with different angles of orientation. The hinge point may be configured such that the position of the portion of the atomizer unit containing the fragrance canister assembly 11 relative to the adapter 9 is adjustable by the user. Alternatively, the portion containing the fragrance canister may be free floating on hinge point 14, such that the relative position of the portion of the atomizer unit containing the fragrance canister assembly is maintained in an upright position due to the forces of gravity.

Figure 5:
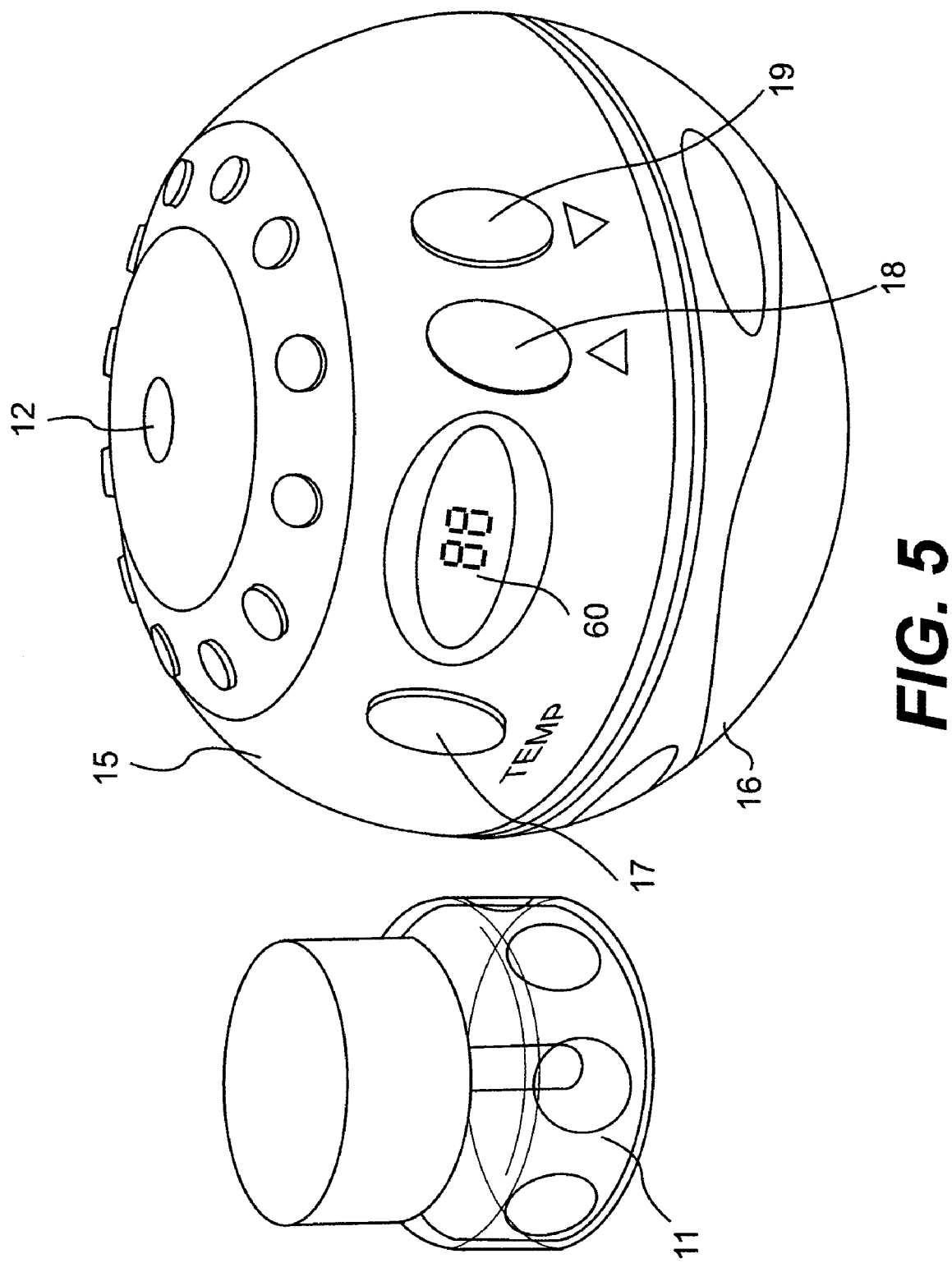
FIG. 5 is a view of a third embodiment of the automobile air freshening system of the present invention.

A third embodiment of the present invention is depicted in FIG. 5. In this embodiment, batteries (not shown) power the atomizer unit. The type of batteries are not particularly limited, and may include, for example, standard AA type batteries or smaller watch style batteries. In this embodiment, the atomizer unit is contained within an upper housing 15 that threadingly engages a lower housing 16. A fragrance canister assembly 11 fits inside the atomizer unit. To insert the fragrance canister assembly 11, the user disengages the lower housing 16 from the upper housing 15. Once separated, the fragrance canister assembly 11 is placed inside the lower housing 16 or attached to the underside of the dome contained in the upper housing 15 by means of a bayonet fitment, snap fitment, screw threads, or any other means to position the fragrance canister assembly and the two housings are again secured together by way of the engagement of the opposing threads or other securing mechanism. Fragrance is then released through a hole 12 in the top of the upper housing.

The embodiment of the atomizer unit depicted in FIG. 5 also contains a temperature sensor (not shown). The temperature sensor allows the atomizer unit to control the delivery rate of the fragrance based on the temperature of the interior airspace of the automobile. Specifically, the temperature sensor senses a temperature and relays the sensed temperature to the controller. The controller compares the relayed temperature with a stored temperature and adjusts the delivery rate of the fragrance according to the results of the comparison.

Use of the temperature sensor is advantageous because, as the temperature of the interior airspace of the automobile increases, the potency of the fragrance also increases. Thus, as the temperature of the interior airspace increases, an air freshening system without a temperature sensor will continue to release fragrance at its usual rate, causing a potentially overwhelming build-up of fragrance. By utilizing a temperature sensor in the embodiment of the present invention depicted in FIG. 5, however, as the temperature of the interior airspace of the automobile increases, the atomizer unit may automatically reduce the delivery rate of the fragrance to compensate for the increase in temperature. In this way, an overwhelming build-up of fragrance within the automobile can be prevented. The atomizer unit may additionally be configured to automatically shut off the atomizer unit if the temperature exceeds a specified threshold temperature.

Referring again to FIG. 5, in this embodiment, the user has the ability to set the temperature at which the atomizer unit will automatically reduce the delivery rate of the fragrance. Specifically, to program the unit of this embodiment, the user first may press temperature setting button 17. Then, the user may select a desired temperature by pressing either a temperature increase button 18 or a temperature decrease button 19 to increase or decrease the temperature displayed on display 60. When display 60 displays the desired temperature, the user again presses the temperature setting button 17 and the temperature selection process ends. Of course, numerous other arrangements could be used to achieve such programmability.

The atomizer unit depicted in FIG. 5 may also be configured with an ON/OFF button (or switch, lever, etc.) mounted into either the lower housing or the upper housing. An ON/OFF button would allow the user the option of turning the temperature sensor off, and have the atomizer unit release fragrance at the pre-determined interval regardless of the temperature of the interior airspace of the automobile.

Additionally, the atomizer unit depicted in FIG. 5 may be equipped with a fragrance intensity selection switch. As described above, a fragrance intensity selection switch would give the user the ability to increase or decrease the frequency at which the atomizer unit releases fragrance.

Figure 6:
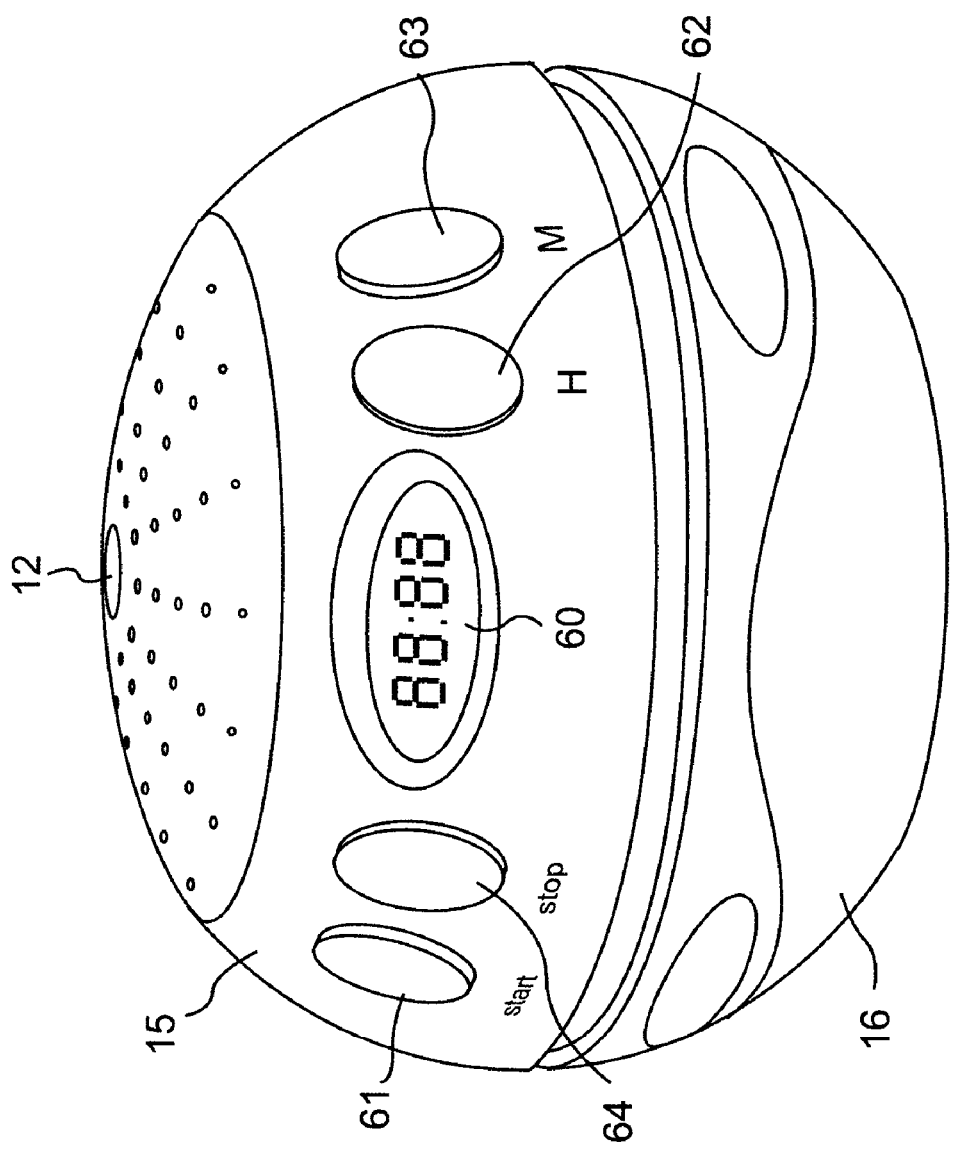
FIG. 6 is a view of a fourth embodiment of the automobile air freshening system of the present invention.
Figure 6:
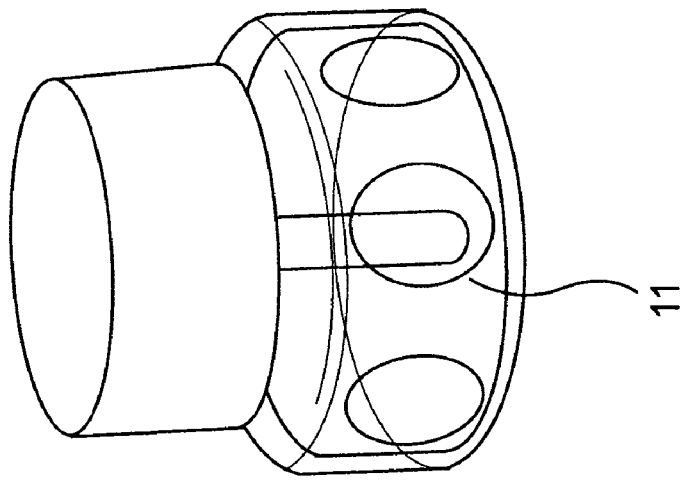

A fourth embodiment of the present invention is depicted in FIG. 6. The design of the fourth embodiment is similar to the third embodiment, and accordingly, components of the fourth embodiment that are identical to the third embodiment are given the same labels.

In the atomizer unit of the fourth embodiment, batteries (not shown) power the atomizer unit. The type of batteries are not particularly limited, and may include, for example, standard AA type batteries or smaller watch style batteries. In this embodiment, the atomizer unit is contained within an upper housing 15 that threadingly engages with a lower housing 16. A fragrance canister assembly 11 fits inside the atomizer unit. To insert the fragrance canister assembly 11, the user disengages the lower housing 16 from the upper housing 15. Once separated, the fragrance canister assembly 11 is placed inside the lower housing 16 and the two housings are again secured together by way of the engagement of the opposing threads, for instance. Fragrance is then released through a hole 12 in the top of the upper housing.

The fourth embodiment of the atomizer unit of the present invention also contains a programming unit comprising start button 61, stop button 64, H button 62, and M button 63. The programming unit gives the user the ability to select, for example, when the atomizer unit will turn on, when the unit will turn off, and how frequently fragrance will be released during the time period between when the unit turns on and when the unit turns off.

The programming unit may be configured for varying levels of complexity. For example, at a basic level, the programming unit would allow the user to set a specific time for the atomizer unit to turn on each day and a specific time at which the atomizer unit would turn off. At a more complex level, the programming unit would give the user, for each day, the ability to select multiple times for the unit to turn on and off and the frequency at which fragrance is released from the unit.

Referring to FIG. 6, operation of a programming unit that allows the user to select a time at which the atomizer unit will turn on and a time at which the atomizer unit will turn off will be described. To set a time at which the atomizer unit will turn on (start time), the user begins by pressing start button 61. Then, the user may press H button 62 to select the hour at which the atomizer unit will turn on and may press M button 63 to select the minute at which the atomizer unit will turn on. When the display 60 displays the desired time, the user again presses the start button 61, ending the start time selection process.

To select a time at which the atomizer unit will turn off (stop time), the user may press stop button 64. Then the user may press H button 62 and M button 63 to select the hour and minute at which the atomizer unit will turn off. When the display 60 displays the desired time, the user again presses the stop button 64, ending the stop time selection process.

Overall, the programming unit works like a conventional alarm clock or setback thermostat. Accordingly, other configurations are possible to achieve the desired degree of programmability.

Additionally, the atomizer unit depicted in FIG. 6 may be equipped with a fragrance intensity selection switch. As described above, a fragrance intensity selection switch would give the user the ability to increase or decrease the frequency at which the atomizer unit releases fragrance.

The programming unit is advantageous because the unit gives the user the ability to conserve fragrance for only the times that the automobile will be used and it can ensure that the automobile is fragranced prior to operation.

An additional feature that may be incorporated into any of the above embodiments is a boost override button. The boost override button may be a separate button (or lever, switch, etc.) mounted into the housing of the atomizer unit, or the feature may be incorporated into one of the buttons already described herein. For example, the boost override button may be incorporated into the fragrance intensity selection switch 13. By pressing the boost override button the user would cause the atomizer unit to contemporaneously release fragrance. In this instance, contemporaneous means at the same time the button is pressed (substantially instantaneously) or at a time following processing of the actuation of the button. Utilization, therefore, of a boost override button would make the atomizer unit dual action; the atomizer unit would provide continuous action by means of its normal periodic release but it would also provide substantially instant action by means of the boost override button. The benefit of the boost override button is that if the user wants to quickly introduce fragrance into the air to override an offending odor or add ambiance, the user can do so.

It should be noted that each of the above-described features of the atomizer unit can be combined with any other, and each and every feature can be incorporated into the atomizer unit regardless of whether the air freshening system is powered by batteries or the 12-volt DC current from the electrical system of the automobile. For example, the atomizer unit may utilize both the temperature sensor and the programming unit. As an additional example, the atomizer unit may utilize the temperature sensor, the programming unit, and the boost override button.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

INDUSTRIAL APPLICABILITY

This invention provides an automobile air freshening system including a piezoelectric atomizer unit and a fragrance canister assembly. We envision that this unit preferably can be used to dispense fragrance into the interior airspace of an automobile to freshen or deodorize the air.

I claim:

1. An automobile air freshening system comprising:
   a piezoelectric atomizer unit for releasing an amount of active ingredient from a canister assembly when the canister assembly is mated therewith;
   a controller for controlling periodic activation of the atomizer unit to release the active ingredient;
   a temperature sensor for sensing a temperature and relaying the sensed temperature to said controller, wherein said controller controls the amount of active ingredient released from said canister based on a comparison between a stored temperature and the sensed temperature;
   a platform serving as a common structural support for both the canister assembly and the piezoelectric atomizer unit; and support prongs that extend from the platform to support a battery.

2. The system according to claim 1, further comprising a programming unit for selectably controlling a time for starting the system and a time for stopping the system, wherein during a time period between the system start time and the system stop time, said controller periodically activates said atomizer unit to release the active ingredient.

3. The system according to claim 2, wherein said programming unit controls the delivery rate of the active ingredient during a time period between the system start time and the system stop time.

4. The system according to claim 1, further comprising a boost override button, which causes said controller to activate said atomizer unit to release the active ingredient contemporaneously with activation of said boost override button.

5. The system according to claim 1, further comprising an active ingredient intensity selection switch for adjusting the frequency at which said controller activates said atomizer unit to release the active ingredient.

6. An automobile air freshening system comprising:
a piezoelectric atomizer unit for releasing an active ingredient from a canister assembly when the canister assembly is mated therewith;
a controller for controlling periodic activation of the atomizer unit such that the active ingredient is released at a specified time interval;
a programming unit for selectably controlling a time for starting the system and a time for stopping the system, wherein during a time period between the system start time and the system stop time, said controller periodically activates said atomizer to release the active ingredient at the specified time intervals;
a platform serving as a common structural support for both the canister assembly and the piezoelectric atomizer unit; and
support prongs that extend from the platform to support a battery.

7. The system according to claim 6, wherein said programming unit controls the delivery rate of the active ingredient during a time period between the system start time and the system stop time.

8. The system according to claim 6, further comprising a boost override button, which causes said controller to activate said atomizer unit to release the active ingredient contemporaneously with actuation of said boost override button.

9. The system according to claim 8, further comprising an active ingredient intensity selection switch for adjusting the frequency at which said controller activates said atomizer unit to release the active ingredient.

* * * * *